(12) United States Patent
Johnson

(10) Patent No.: US 8,124,849 B2
(45) Date of Patent: Feb. 28, 2012

(54) SQUASH LINE YPC 130-1035T

(75) Inventor: William C. Johnson, Sacramento, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 187 days.

(21) Appl. No.: 12/197,816

(22) Filed: Aug. 25, 2008

(65) Prior Publication Data

US 2009/0064364 A1 Mar. 5, 2009

Related U.S. Application Data

(60) Provisional application No. 60/968,873, filed on Aug. 29, 2007.

(51) Int. Cl.
*A01H 5/00* (2006.01)
*A01H 5/10* (2006.01)
*A01H 1/00* (2006.01)
*C12N 15/82* (2006.01)
*C12N 5/04* (2006.01)
*C12Q 1/68* (2006.01)

(52) U.S. Cl. ....... 800/310; 435/410; 435/6.11; 800/260; 800/278

(58) Field of Classification Search .................. None
See application file for complete search history.

(56) References Cited

U.S. PATENT DOCUMENTS

| | | | |
|---|---|---|---|
| 4,713,491 A | 12/1987 | Adams | 800/1 |
| 5,457,278 A | 10/1995 | Majchrowski | 800/200 |
| 5,811,642 A | 9/1998 | Stracheljahn | 800/200 |
| 5,998,699 A | 12/1999 | Slightom et al. | 800/205 |
| 6,031,158 A | 2/2000 | Miller et al. | 800/310 |
| 6,337,431 B1 * | 1/2002 | Tricoli et al. | 800/280 |
| 6,414,224 B1 | 7/2002 | Superak | 800/310 |
| 6,916,974 B2 * | 7/2005 | Superak et al. | 800/310 |
| 2007/0056059 A1 | 3/2007 | Johnson et al. | 800/301 |

OTHER PUBLICATIONS

"Availability of Determination of nonregulated status for virus resistant squash," Animal and Plant Health Inspection Service, USDA, Federal Register, 59(238):64187-64189, Dec. 13, 1994.

Fuchs et al., "Resistance of transgenic hybrid squash ZW-20 expressing the coat protein genes of zucchini yellow mosaic virus and watermelon mosaic virus 2 to mixed infections by both potyviruses," *Bio/Technology*, 13:1466-1473, 1995.

Pang et al., "Resistance to squash mosaic comovirus in transgenic squash plants expressing its coat protein genes," *J. Molecular Breeding*, 6(1):87-93, 2000.

* cited by examiner

*Primary Examiner* — Anne Kubelik
(74) *Attorney, Agent, or Firm* — SNR Denton US LLP; Alissa Eagle Esq

(57) ABSTRACT

The invention provides seed and plants of the squash line designated YPC 130-1035T. The invention thus relates to the plants, seeds and tissue cultures of squash line YPC 130-1035T, and to methods for producing a squash plant produced by crossing a plant of squash line YPC 130-1035T with itself or with another squash plant, such as a plant of another line. The invention further relates to seeds and plants produced by such crossing. The invention further relates to parts of a plant of squash line YPC 130-1035T, including the fruit and gametes of such plants.

26 Claims, No Drawings

SQUASH LINE YPC 130-1035T

This application claims the priority of U.S. Provisional Appl. Ser. No. 60/968,873, filed Aug. 29, 2007, the entire disclosure of which is incorporated herein by reference.

BACKGROUND OF THE INVENTION

1. Field of the Invention

The present invention relates to the field of plant breeding and, more specifically, to the development of squash line YPC 130-1035T.

2. Description of Related Art

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is squash. The term squash is used to refer to four species of the genus *Cucurbita* of the family Cucurbitaceae: (1) *C. maxima*, which includes the Hubbard, buttercup, and some large pumpkins, (2) *C. mixta*, including cushaw squash, (3) *C. moschata*, which includes the butternut squash, and (4) *C. pepo*. Acorn squash, zucchini, yellow crookneck and straightneck, and most pumpkins belong to this last species.

The term squash encompasses pumpkins, marrows, and zucchinis. Exclusively ornamental and functional varieties are included among gourds. There is considerable variation in size, shape and color. A typical categorization is to distinguish between summer and winter varieties. Summer squashes include young vegetable marrows, such as zucchini, and are harvested during the summer months. At this stage, the skin of the fruit is tender and the fruit relatively small. Common fruit forms include straightneck, crookneck, saucer shaped, and oblong.

Winter squashes, including Hubbard, butternut and pumpkin, are harvested in late summer/early Fall once the rind has hardened. In contrast to summer squash, winter squash is eaten in the mature fruit stage. In some regions the term 'winter squash' is used to refer to mature fruits of the *maxima* species only.

Many different squash cultivars have been produced, and squash breeding efforts have been underway in many parts of the world (see e.g. U.S. Pat. No. 6,916,974, U.S. Pat. No. 6,414,224, U.S. Pat. No. 5,811,642, U.S. Pat. No. 5,457,278, U.S. Pat. No. 4,713,491). Some breeding objectives include varying the color, texture and flavor of the fruit. Other objectives include optimizing flesh thickness, solid content (% dry matter), and sugar content. Breeding programs have also focused on developing plants with earlier fruit maturity, more restricted vine growth, improved disease resistance or tolerance, and improved adaptability to environmental conditions. In the case of pumpkins, one goal is to produce hull-less seeds for the snack food industry. In the case of summer squash, one of the goals is to develop plants with reduced prickly spines. A parthenocarpic hybrid summer squash has been reported (U.S. Pat. No. 6,031,158).

Advances in biotechnology have resulted in genetically engineered squash with resistance or immunity to some viruses. One of the earliest examples is a squash line having resistance to zucchini yellow mosaic virus and watermelon mosaic virus 2 (Fuchs et al., 1995). Development of transgenic squash that is resistant to SqMV and other viruses has also been reported (Pang et al., 2000; U.S. Pat. No. 6,337, 431).

While breeding efforts to date have provided a number of useful squash lines with beneficial traits, there remains a great need in the art for new lines with further improved traits. Such plants would benefit farmers and consumers alike by improving crop yields and/or quality.

SUMMARY OF THE INVENTION

In one aspect, the present invention provides a squash plant of the line designated YPC 130-1035T. Also provided are squash plants having all the physiological and morphological characteristics of the squash line designated YPC 130-1035T. Parts of the squash plant of the present invention are also provided. For example, these include a pollen grain, an ovule, a scion, a rootstock, a fruit, and a cell of the plant.

The invention also concerns seed of squash line YPC 130-1035T. The squash seed of the invention may be provided as an essentially homogeneous population of squash seed of the line designated YPC 130-1035T. Essentially homogeneous populations of seed are generally free from substantial numbers of other seed. Therefore, seed of line YPC 130-1035T may be defined as forming at least about 97% of the total seed, including at least about 98%, 99%, or more of the seed. The population of squash seed may be particularly defined as being essentially free from hybrid seed. The seed population may be separately grown to provide an essentially homogeneous population of squash plants designated YPC 130-1035T.

In another aspect of the invention, a plant of squash line YPC 130-1035T comprising an added heritable trait is provided. The heritable trait may comprise a genetic locus that is, for example, a dominant or recessive allele. In one embodiment of the invention, a plant of squash line YPC 130-1035T is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line YPC 130-1035T is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line YPC 130-1035T include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides squash plants regenerated from a tissue culture of the invention, the plants having all the physiological and morphological characteristics of line YPC 130-1035T.

In yet another aspect of the invention, processes are provided for producing squash seeds, plants and fruit, which processes generally comprise crossing a first parent squash plant with a second parent squash plant, wherein at least one of the first or second parent squash plants is a plant of the line designated YPC 130-1035T. These processes may be further exemplified as processes for preparing hybrid squash seed or plants, wherein a first squash plant is crossed with a second squash plant of a different, distinct line to provide a hybrid that has, as one of its parents, the squash plant line YPC 130-1035T. In these processes, crossing will result in the production of seed. The seed production occurs regardless of whether the seed is collected or not.

In one embodiment of the invention, the first step in "crossing" comprises planting seeds of a first and second parent squash plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent squash plants into plants that bear flowers. A third step may comprise preventing self-pollination of the plants, such as by emasculating the male flowers, (i.e., treating or manipulating the flowers to produce an emasculated parent squash plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent squash plants. Yet another step comprises harvesting the seeds from at least one of the parent squash plants. The harvested seed can be grown to produce a squash plant or hybrid squash plant.

The present invention also provides the squash seeds and plants produced by a process that comprises crossing a first parent squash plant with a second parent squash plant, wherein at least one of the first or second parent squash plants is a plant of the line designated YPC 130-1035T. In one embodiment of the invention, squash seed and plants produced by the process are first generation ($F_1$) hybrid squash seed and plants produced by crossing a plant in accordance with the invention with another, distinct plant. The present invention further contemplates plant parts of such an $F_1$ hybrid squash plant, and methods of use thereof. Therefore, certain exemplary embodiments of the invention provide an $F_1$ hybrid squash plant and seed thereof.

In still yet another aspect of the invention, the genetic complement of the squash plant line designated YPC 130-1035T is provided. The phrase "genetic complement" is used to refer to the aggregate of nucleotide sequences, the expression of which sequences defines the phenotype of, in the present case, a squash plant, or a cell or tissue of that plant. A genetic complement thus represents the genetic makeup of a cell, tissue or plant, and a hybrid genetic complement represents the genetic make up of a hybrid cell, tissue or plant. The invention thus provides squash plant cells that have a genetic complement in accordance with the squash plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line YPC 130-1035T or a first generation progeny thereof could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by squash plant cells, tissues, plants, and seeds, formed by the combination of a haploid genetic complement of a squash plant of the invention with a haploid genetic complement of a second squash plant, preferably, another, distinct squash plant. In another aspect, the present invention provides a squash plant regenerated from a tissue culture that comprises a hybrid genetic complement of this invention.

In still yet another aspect, the invention provides a plant of an inbred squash line that exhibits resistance to Zucchini Yellow Mosaic Virus (ZYMV), Watermelon Mosaic Virus (WMV), Cucumber Mosaic Virus, and/or Papaya Ringspot Virus (PRSV). In certain embodiments, the trait may be defined as controlled by genetic means for the expression of the trait found in squash line YPC 130-1035T.

In still yet another aspect, the invention provides a method of determining the genotype of a plant of squash line YPC 130-1035T comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line YPC 130-1035T, the method comprising the steps of: (a) preparing a progeny plant derived from line YPC 130-1035T, wherein said preparing comprises crossing a plant of the line YPC 130-1035T with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line YPC 130-1035T. The plant derived from line YPC 130-1035T may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line YPC 130-1035T is obtained which possesses some of the desirable traits of the line as well as potentially other selected traits.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of squash line YPC 130-1035T. This line shows uniformity and stability within the limits of environmental influence for the traits described hereinafter and provides sufficient seed yield. By crossing with a distinct and homozygous second plant, uniform F1 hybrid progeny can be obtained.

Line YPC 130-1035T exhibits a number of improved traits including resistance to Zucchini Yellow Mosaic Virus (ZYMV), Watermelon Mosaic Virus (WMV), Cucumber Mosaic Virus, and/or Papaya Ringspot Virus (PRSV). The development of the line can be summarized as follows.

A. Origin and Breeding History of Squash Line YPC 130-1035T

Squash line YPC 130-1035T was developed by a selection strategy involving two components: (1) "Cougar"—a commercial hybrid sold by Harris Moran Seed Company having intermediate level resistance to ZYMV and PRSV, and good agronomic fruit traits and an extended harvest, and (2) "TS960218BBAB"—an advanced generation Seminis proprietary breeding line of precocious yellow straightneck squash having excellent fruit length, earliness, and carrying the CZW3 transgene. The initial cross was made in a greenhouse in California in the fall season, 2001.

Because a parent of this population is a hybrid, the F1 generation was segregating for a number of traits. This population was grown and selected in 3 separate environments in 2002, and 24 unique F2 populations were created. The lineage from which YPC 130-1035T was derived was selected in Florida in the spring of 2002 in the open field, and self pollinated. All available seed of the F2 generation selections were sown in the greenhouse in California in spring 2002, approximately 1400 seedlings total, where they were manually inoculated with ZYMV, CMV, and PRSV. The 589 seedlings showing the highest level of resistance to foliar symptoms of virus infection were transplanted to the open field, where 2 selections were made in the lineage from which YPC 130-1035T was derived. The F3 generation from which YPC 130-1035T was derived was sown in the fall season, 2002 in the same Florida location, concurrently with a screening generation performed in a greenhouse in California, where seedlings of each family were observed for their reaction to inoculation with PRSV and CMV. Results of the virus screening were combined with observation of fruit quality characteristics and growth habit observations in Florida, resulting in 12 F4 selections. 60 seeds for each of the available F4 selections were sown in the early spring of 2003 in Felda, Fla., where they were again inoculated at the seedling stage with a cocktail including ZYMV, WMV, and PRSV. Six selections were advanced to the F5 generation.

Beginning in the F5 generation, evaluation of these breeding lines was based on both performance of the breeding lines and performance of hybrids created using these breeding lines. For the lineage that became YPC 130-1035T, the F5 generation was self pollinated during the 2004 early spring greenhouse cycle in California, concurrently with the production of 5 test hybrids. During the subsequent 3 years, more than 10 genetically unique hybrids have been created and evaluated using this lineage. Comparisons of these hybrids to commercial standards have been performed in at least 10 states. Hybrids using YPC 130-1035T show good horticultural characteristics, field tolerance to PRSV, and resistance to many strains of ZYMV, WMV, and CMV.

Two additional generations of advancement were completed in 2004 through self pollination of greenhouse and field grown plants. These additional generations insure uniformity of the parental line, and the initial stock to found the population of YPC 130-1035T was based on a bulk of seed from 7 F8 generation plants with the same F7 generation presource. The pedigree and lineage of this F8 generation is (Cougar/TS960218BBAB)-4-2-2-1-8-1-M.

YPC 130-1035T has a complement of resistance traits and horticultural characteristics that make it ideal for many purposes, including for production of precocious yellow hybrids adapted to the United States. YPC 130-1035T may also be useful in the development of hybrids for other markets once the transgenic virus resistance is approved for wider use.

B. Physiological and Morphological Characteristics of Squash Line YPC 130-1035T

In accordance with one aspect of the present invention, there is provided a plant having the physiological and morphological characteristics of squash line YPC 130-1035T. A description of the physiological and morphological characteristics of squash line YPC 130-1035T is presented in Table 1.

TABLE 1

Physiological and Morphological Characteristics of Line YPC 130-1035T

| CHARACTERISTIC | YPC 130-1035T |
|---|---|
| 1. General Descriptors | |
| Fruit Shape/Variety Group | Straightneck |
| Expected Primary Usage | Culinary |
| Parts of Plant Providing Expected Primary Usage | Immature Fruit |
| Cotyledons Measured Between Full Expansion of $1^{st}$ and $2^{nd}$ True Leaves | Length to Width Ratio - 1.95<br>Apex - Not Notched<br>Veining - Obvious |
| 2. Main Stem | |
| Main Color | Dark Green (Nearly Entire Length - Multipik, Jack O'Lantern, Howden) |
| White Marks at Nodes | Absent |
| Yellow Marks (Associated with Precocious Yellow Gene Complex) | Present |
| Growth Habit (20 True Leaves) | |
| Bush | True-bush (Multipik, Cocozelle, Ronde de Nice, Benning's Green Tint) |
| Tendrils (20 True Leaves) | Present and Elongated |
| Main Stem Internode Dimensions Observed after $20^{th}$ Internode Developed | |
| Length | Increases from $5^{th}$ to $15^{th}$ Internode |
| Width | Decreases from $5^{th}$ to $15^{th}$ Internode |
| 3. Petioles | |
| Derived from Main Stem Observed after $20^{th}$ Node Developed | |
| Length to Medial Width Ratio of 10th | 35.23 |
| Length to Medial Width Ratio of $15^{th}$ Petiole | 38.43 |
| Spininess (Prickles) Observed after $20^{th}$ Internode | Slightly Spiny (Goldy, Multipik) |
| Angle of $6^{th}$ through $15^{th}$ on Main Stem | Horizontal (Caserta, less than 10°) |
| 4. Laminae | |
| Lobing of $10^{th}$ and $15^{th}$ on Main Stem | Medium Lobed |
| Dimensions of Leaf after $20^{th}$ Internode | 0.83 Length to Maximal Width Ratio of $10^{th}$ True Leaf |
| Dimensions of Leaf after $20^{th}$ Internode | 0.81 Length to Maximal Width ratio of $15^{th}$ True Leaf |
| Silver Blotching or Mottling | Silver Blotching Absent (Costata Romanesca, Early Prolific Straightneck) |
| 5. Flowers | |
| Number per Node | Often More than One |
| Staminate on day of Anthesis on Main Stem (Between Nodes 11/20) | |
| Length from Base of Calyx to Tip of Corolla | 94.3 mm |
| Exterior Width at Top of Calyx Cup | 12.5 mm |
| Pedicel Length | 187.3 mm |
| Length of Anther Column | 11.7 mm |
| Dominant Color of Corolla of Staminate Flower | Orange-yellow (Day of Anthesis) |
| Ring at Base of Interior of Staminate Corolla | Absent |
| Ring at Base of Interior of Pistillate Corolla | Yellow |
| Pistillate Flower on Day of Anthesis | |
| Length from Base of Calyx to Tip of Corolla | 87.8 mm |
| Pedicel Length | 41.5 mm |
| Ovary Color (Day Prior to Anthesis) | Yellow (Goldy Gold Rush, Multipik) |
| 6. Immature Fruit | |
| Size (3-5 Days Past Anthesis) | |
| Length (through Axis) to Medial Width Ratio | 4.23 |
| Length (through Axis) to Maximal Width Ratio | 3.73 |

TABLE 1-continued

Physiological and Morphological Characteristics of Line YPC 130-1035T

| CHARACTERISTIC | YPC 130-1035T |
|---|---|
| Color (3-5 Days Past Anthesis) | Light Yellow (Early Prolific Straightneck, Yellow Summer Crookneck, Multipik, Dixie, Gentry) |
| Fruit Flecks | Small (Nero di Milano, Raven, Magic Lantern) |
| Fruit Warting | Absent (Cocozelle, Multipik, Ronde de Nice, Gentry) |

*These are typical values. Values may vary due to environment. Other values that are substantially equivalent are also within the scope of the invention.

Line YPC 130-1035T has been self-pollinated and planted for a number of generations to produce the homozygosity and phenotypic stability to make this line useful in commercial seed production. No variant traits have been observed or are expected for this line. Squash line YPC 130-1035T, being substantially homozygous, can be reproduced by planting seeds of the line, growing the resulting squash plant under self-pollinating or sib-pollinating conditions and harvesting the resulting seeds using techniques familiar to one of skill in the art.

C. Breeding Squash Line YPC 130-1035T

One aspect of the current invention concerns methods for crossing the squash line YPC 130-1035T with itself or a second plant and the seeds and plants produced by such methods. These methods can be used for propagation of line YPC 130-1035T, or can be used to produce hybrid squash seeds and the plants grown therefrom. Hybrid seeds are produced by crossing line YPC 130-1035T with second squash parent line.

The development of new varieties using one or more starting varieties is well known in the art. In accordance with the invention, novel varieties may be created by crossing line YPC 130-1035T followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line YPC 130-1035T and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with YPC 130-1035T for the purpose of developing novel squash lines, it will typically be preferred to choose those plants which either themselves exhibit one or more selected desirable characteristics, or which exhibit the desired characteristic(s) when in hybrid combination. Examples of desirable characteristics related to the rind of the fruit include: a certain coloring, striping, firmness and texture. Desirable characteristics related to the flesh of the fruit include: a certain flavor, taste, texture, thickness, color, sugar content, and solids content (% dry matter). Another desirable set of traits related to the fruit include: a certain fruit size and shape. Other desirable characteristics include: high fruit yield, early maturity, restricted vine growth, improved seed germination, and high seed yield. Disease resistance or tolerance, especially to the diseases mentioned above and throughout this application, is another desirable characteristic. Desirable characteristics related to the environment include: tolerance to environmental stress (e.g. frost, drought, etc.) and adaptability to a wide variety of environmental conditions (e.g. soil, temperature, moisture, etc.). In the case of pumpkins, a desired trait is producing hull-less seeds. In the case of summer squash, an additional desired trait is the absence of spines.

D. Performance Characteristics

As described above, line YPC 130-1035T exhibits desirable horticultural traits, including resistance to ZYMV, WMV, CMV, and PRSV. In addition, hybrids made using YPC 130-1035T as a parent line also demonstrate multivirus resistance, along with other desirable horticultural traits. Hybrids made with the line were the subject of objective analysis of performance traits of a hybrid made using YCN 130-1053T compared to other precocious yellow straightneck cultivars. The results of the analysis are presented below in Table 2. During the year and at the location where this analysis was performed, natural incidence of viral diseases was unusually low, so that resistance levels for ZYMV, WMV, CMV, and PRSV were not observable in this trial. As the truly unique and valuable feature of hybrids derived from YPC 130-1035T is their multivirus resistance, the horticultural characteristics of these lines need only match those of a typical commercial product to demonstrate value to the farmer.

TABLE 2

Horticultural Scoring of Precocious Yellow Straightneck Hybrid Using YPC 130-1035T Compared To Those Commercially Important Cultivars Not Produced Using YPC 130-1035T

| Cultivar | YPC 130-1035T Hybrid | DTM | Spines | Blossom SCAR | Fruit Uniformity | Gloss | Fruit Color | Fruit Shape | PM Res |
|---|---|---|---|---|---|---|---|---|---|
| Multipik | No | 35 | 8 | 7 | 4 | 4 | 3 | 4 | 7 |
| SUNRAY | No | 39 | 7 | 6 | 5 | 3 | 2 | 3 | 3 |
| General Patton | No | 38 | 7 | 5 | 6 | 4 | 3 | 3 | 6 |
| XPT 1832 III | No | 36 | 7 | 5 | 5 | 4 | 3 | 3 | 7 |
| SVT 13045861 III | Yes | 38 | 6 | 5 | 3 | 2 | 3 | 2 | 7 |

Cultivar describes the commercial or pre-commercial name of the hybrid being evaluated. YPC 130-1035T Hybrid describes whether the cultivar being evaluated uses the parent in question in production of the cultivar. DTM describes the approximate number of days from sowing to harvest maturity in the trial where these cultivars were evaluated. Remaining traits are rated on a 1 to 9 scale, with 1 being ideal and 9 being completely unacceptable. Spines represents the relative size and number of epidermal spines on the plant which can damage fruit during harvest, where 1 is a spineless plant and 9 is an excessively spiny plant. Blossom Scar represents the relative size of the blossom scar, where a rating of 1 is for a tiny and inconspicuous blossom scar, and 9 is a very large and protruding blossom scar. Fruit uniformity describes the overall level of variation for harvested fruit size, shape, color, and weight, where a rating of 1 represents a high level of uniformity in harvest stage fruit and 9 represents wide variation in size, color, and shape of fruits. Gloss represents the level of glossiness or shininess of the harvested fruit, where 1 is a very high level of relative light reflectance and 9 is a dull and non-reflecting fruit surface. Fruit Color represents the average color of the fruits, where 1 is an intensely yellow color and 9 is unusually pale or darkly colored fruit. Fruit shape represents how well the fruit conforms to an ideal shape for the type, and in the case of precocious yellow straightneck cultivars a rating of 1 is a non-curving cylindrical fruit which may be tapered but lacks obvious bulbing or protrusions, and a rating of 9 is for curved, bulbous, and/or non-cylindrical fruit shapes. PM Res represents the level of natural infestation by the Powdery Mildew fungus, where 1 is complete absence of infestation symptoms, 3 is a high level of resistance (minimal evidence of easily visible fungal growth), 5 is an intermediate level of resistance (field tolerance, moderate fungal growth mostly limited to older leaves), 7 is a very low level of resistance (only the youngest leaves show temporary absence of fungal growth), and 9 is complete coverage of all aboveground tissues by fungal infestation.

As shown above, the hybrid using line YPC 130-1035T exhibits superior fruit shape, fruit uniformity and fruit glossiness when compared to competing cultivars. One important aspect of the invention thus provides seed of the variety for commercial use.

E. Further Embodiments of the Invention

When the term squash line YPC 130-1035T is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those squash plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental squash plant which contributes the locus for the desired characteristic is termed the nonrecurrent or donor parent. This terminology refers to the fact that the nonrecurrent parent is used one time in the backcross protocol and therefore does not recur. The parental squash plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a squash plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny squash plants of a backcross in which YPC 130-1035T is the recurrent parent comprise (i)

the desired trait from the non-recurrent parent and (ii) all of the physiological and morphological characteristics of squash line YPC 130-1035T as determined at the 5% significance level when grown in the same environmental conditions. Squash varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of squash plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of squash are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Squash Line YPC 130-1035T by Genetic Engineering

Many useful traits that can be introduced by backcrossing, as well as directly into a plant, are those which are introduced by genetic transformation techniques. Genetic transformation may therefore be used to insert a selected transgene into the squash line of the invention or may, alternatively, be used for the preparation of transgenes which can be introduced by backcrossing. Methods for the transformation of plants, including squash, are well known to those of skill in the art. Techniques which may be employed for the genetic transformation of squash include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. Microprojectile bombardment techniques are widely applicable, and may be used to transform virtually any plant species. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target squash cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

*Agrobacterium*-mediated transformation of squash explant material and regeneration of whole transformed squash plants has been shown to be an efficient transformation method (U.S. Pat. No. 6,337,431). An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for squash plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the squash lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a squash plant according to the invention. Non-limiting examples of particular genes and corresponding phenotypes one may choose to introduce into a squash plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a squash variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a squash plant by transformation.

Triploid: A cell or organism having three sets of chromosomes.

H. Deposit Information

A deposit of squash line YPC 130-1035T, disclosed above and recited in the claims, has been made with the American Type Culture Collection (ATCC), 10801 University Blvd., Manassas, Va. 20110-2209. The date of deposit was Apr. 30, 2007. The accession number for those deposited seeds of squash line YPC 130-1035T is ATCC Accession No. PTA-8395. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 4,713,491
U.S. Pat. No. 5,378,619
U.S. Pat. No. 5,457,278
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,811,642
U.S. Pat. No. 5,880,275
U.S. Pat. No. 6,031,158
U.S. Pat. No. 6,337,431
U.S. Pat. No. 6,414,224
U.S. Pat. No. 6,916,974
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Fuchs et al., *Bio/Technology*, 13:1466 73, 1995.
Gibson and Shillito, *Mol. Biotech.*, 7:125,1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Pang et al., *J. Molecular Breeding*, 6(1):87-93, 2000
PCT Appln. WO 99/31248
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.

What is claimed is:

1. A seed of squash line YPC 130-1035T, a sample of seed of said line having been deposited under ATCC Accession Number PTA-8395.

2. A plant of squash line YPC 130-1035T, a sample of seed of said line having been deposited under ATCC Accession Number PTA-8395.

3. A plant part of the plant of claim 2.

4. The plant part of claim 3, wherein said part is selected from the group consisting of a leaf, fruit, pollen, rootstock, scion, an ovule and a cell.

5. A squash plant, or a part thereof, having all the physiological and morphological characteristics of the squash plant of claim 2.

6. A tissue culture of regenerable cells of squash line YPC 130-1035T, a sample of seed of said line having been deposited under ATCC Accession Number PTA-8395.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A squash plant regenerated from the tissue culture of claim 6, wherein the regenerated plant expresses all of the physiological and morphological characteristics of squash line YPC 130-1035T, a sample of seed of said line having been deposited under ATCC Accession Number PTA-8395.

9. A method of producing squash seed, said method comprising crossing the plant of claim 2 with a second squash plant.

10. The method of claim 9, wherein the plant of squash line YPC 130-1035T is the female parent.

11. The method of claim 9, wherein the plant of squash line YPC 130-1035T is the male parent.

12. An F1 hybrid seed produced by the method of claim 9.

13. An F1 hybrid plant produced by growing the seed of claim 12.

14. A method for producing a seed of a line YPC 130-1035T-derived squash plant, said method comprising the steps of:
 (a) crossing a squash plant of line YPC 130-1035T, a sample of seed of said line having been deposited under ATCC Accession Number PTA-8395, with a second squash plant; and
 (b) allowing seed of a YPC 130-1035T-derived squash plant to form.

15. The method of claim 14, further comprising the steps of:
 (c) crossing a plant grown from said YPC 130-1035T-derived squash seed with itself or a second squash plant to yield additional YPC 130-1035T-derived squash seed;
 (d) growing said additional YPC 130-1035T-derived squash seed of step (c) to yield additional YPC 130-1035T-derived squash plants; and
 (e) repeating the crossing and growing steps of (c) and (d) to generate further YPC 130-1035T-derived squash plants.

16. A method of vegetatively propagating a plant of squash line YPC 130-1035T, said method comprising the steps of:
 (a) collecting tissue capable of being propagated from a squash plant of line YPC 130-1035T, a sample of seed of said line having been deposited under ATCC Accession Number PTA-8395;
 (b) cultivating said tissue to obtain proliferated shoots; and
 (c) rooting said proliferated shoots to obtain rooted plantlets.

17. The method of claim 16, further comprising growing plants from said rooted plantlets.

18. A method of introducing a desired trait into squash line YPC 130-1035T, said method comprising:
 (a) crossing a plant of line YPC 130-1035T, a sample of seed of said line having been deposited under ATCC Accession Number PTA-8395, with a second squash plant that comprises a desired trait to produce F1 progeny;
 (b) selecting an F1 progeny that comprises the desired trait;
 (c) crossing the selected F1 progeny with a plant of line YPC 130-1035T to produce backcross progeny;
 (d) selecting backcross progeny comprising the desired trait and the physiological and morphological characteristic of squash line YPC 130-1035T; and
 (e) repeating steps (c) and (d) three or more times in succession to produce selected fourth or higher backcross progeny that comprise the desired trait.

19. A squash plant produced by the method of claim 18.

20. A method of producing a plant of squash line YPC 130-1035T, a sample of seed of said line having been deposited under ATCC Accession Number PTA-8395, comprising an added desired trait, the method comprising introducing a transgene conferring the desired trait into a plant of squash line YPC 130-1035T.

21. A plant that comprises all of the physiological and morphological characteristics of squash line YPC 130-1035T, a sample of seed of said line having been deposited under ATCC Accession Number PTA-8395.

22. A seed that produces the plant of claim 21.

23. A method of determining the genotype of the plant of claim 2 or a first generation progeny thereof, said method comprising obtaining a sample of nucleic acids from said plant and detecting in said nucleic acids a plurality of polymorphisms.

24. The method of claim 23, further comprising storing the results of detecting the plurality of polymorphisms on a computer readable medium.

25. A method of producing squash, said method comprising:
 (a) obtaining the plant of claim 2, wherein the plant has been cultivated to maturity; and
 (b) collecting squash from the plant.

26. A squash plant produced by the method of claim 20.

* * * * *